US00PP35271P2

(12) United States Plant Patent
Bergman

(10) Patent No.: US PP35,271 P2
(45) Date of Patent: Jul. 18, 2023

(54) ***CHRYSANTHEMUM* PLANT NAMED 'CIDZ0118'**

(50) Latin Name: *Chrysanthemum x morifolium*
Varietal Denomination: CIDZ0018

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/108,115

(22) Filed: Feb. 10, 2023

(51) Int. Cl.
*A01H 5/02* (2018.01)
*A01H 6/14* (2018.01)

(52) U.S. Cl.
USPC ..... Plt./295

(58) Field of Classification Search
USPC ..... Plt./286, 295
See application file for complete search history.

*Primary Examiner* — Susan McCormick Ewoldt
(74) *Attorney, Agent, or Firm* — Dale Skalla

(57) ABSTRACT

A new *Chrysanthemum* plant named 'CIDZ0118' particularly distinguished by its yellow daisy-type inflorescences, excellent flower production, strong vigorous growth and spreading plant habit, and very uniform flowering with response time of 7.5 weeks when grown under short days.

1 Drawing Sheet

Latin name of the genus and species of the plant claimed: *Chrysanthemum* x *morifolium.*

Varietal denomination: 'CIDZ0118'.

BACKGROUND OF THE NEW PLANT

The present invention comprises a new *Chrysanthemum*, botanically known as *Chrysanthemum* x *morifolium*, and hereinafter referred to by the variety name 'CIDZ0118'.

'CIDZ0118' is a product of a planned breeding program. The new cultivar has yellow daisy-type inflorescences, excellent flower production, strong vigorous growth and spreading plant habit, and very uniform flowering with response time of 7.5 weeks when grown under short days.

'CIDZ0118' originates as a natural whole plant mutation discovered among flowering plants of 'CIDZ0066" growing in a greenhouse in Gilroy, Calif. in July 2018.

The parent 'CIDZ0066', U.S. Plant Pat. No. 27,406, sold commercially as 'Grandview Light Pink', having inflorescences of a pale pink hue under usual conditions, while it is similar to 'CIDZ0118' in all other characteristics.

The first act of asexual reproduction of 'CIDZ0118' was accomplished when vegetative stem cuttings were propagated from the initial selection in November 2018 in a greenhouse in Gilroy, Calif.

BRIEF SUMMARY OF INVENTION

Horticultural examination of plants grown from cuttings of the plant initiated February, 2019, and continuing thereafter, has demonstrated that the combination of characteristics as herein disclosed for 'CIDZ0118' are firmly fixed and are retained through successive generations of asexual reproduction.

'CIDZ0118' has not been observed under all possible environmental conditions. The phenotype may vary significantly with variations in environment such as temperature, light intensity and day length.

A Plant Breeder's Right for this cultivar has not yet been applied for. 'CIDZ0118' has not been made publicly available prior to the effective filing date of this application, notwithstanding any disclosure that may have been made less than one year prior to the effective filing date of this application by the inventor or another who obtained 'CIDZ0118' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0118' with colors being as true as possible with an illustration of this type.

Figure 1:
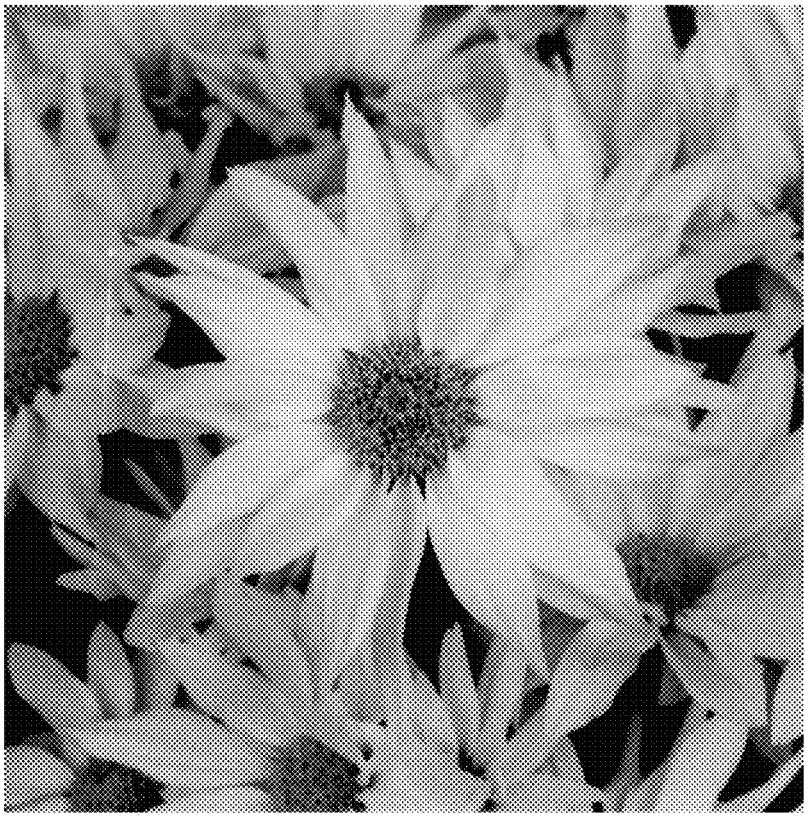
Figure 2:
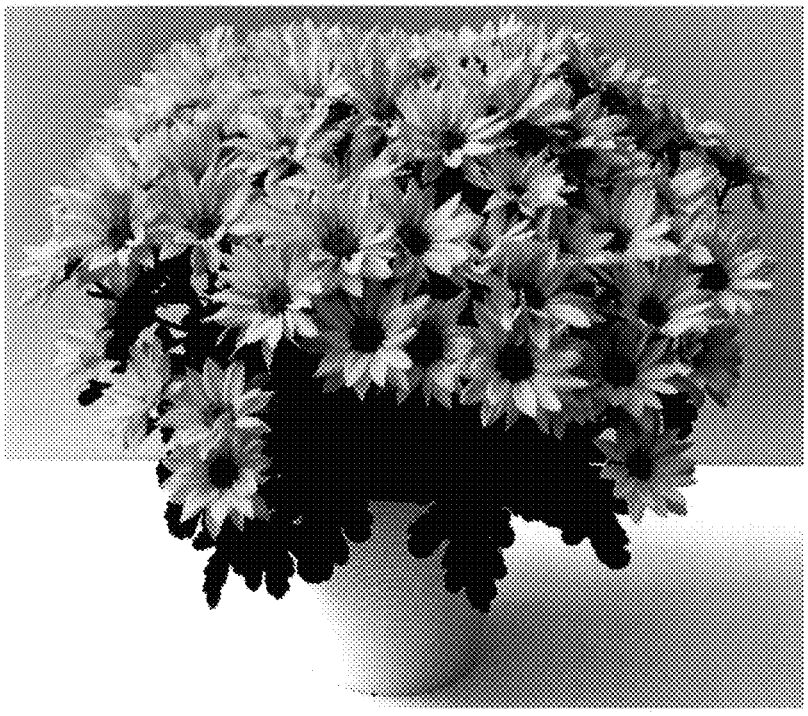

The photographic drawings, taken in Gilroy, Calif. in August 2021, show in FIG. 1 a close-up view of the inflorescence of the new variety and in FIG. 2 a whole flowering plant.

DETAILED BOTANICAL DESCRIPTION

The plant descriptions and measurements were taken indoors in Gilroy, Calif. in November 2022 on about 11 weeks old plants. Unrooted cuttings had been planted, 4 plants per pot, in 6 inch pots in August 2022. The plants were pinched and moved to short days in September 2022 to induce flowering.

Color references are made to The Royal Horticultural Society Colour Chart (RHS) 2001.

TABLE 1

DIFFERENCES BETWEEN THE NEW VARIETY 'CIDZ0118' AND A MOST SIMILAR VARIETY:

| | 'CIDZ0118' | 'Yochesapeake', U.S. Plant Pat. No. 12,535 |
|---|---|---|
| Plant height: | Shorter | Taller |
| Flower color: | Medium yellow | Stronger yellow |
| Flowering response: | Faster | Slower |

Plant:
- *Form, growth and habit.*—Herbaceous pot-type, stems upright, freely branching, strong and moderately vigorous growth habit.
- *Plant height.*—18 cm.
- *Plant height (inflorescence included).*—21 cm.
- *Plant width.*—39 cm.

Roots:
- *Number of days to initiate roots.*—4 days at about 22 degrees C.
- *Number of days to produce a rooted cutting.*—10-12 days at 22 degrees C.
- *Type.*—Fine, fibrous, free branching.
- *Color.*—RHS N155B but whiter.

Foliage:
- *Arrangement.*—Alternate.
- *Immature, leaf color, upper surface.*—RHS 137B.
- *Lower surface.*—RHS 137C.
- *Mature, leaf color, upper surface.*—RHS 137A.
- *Lower surface.*—RHS 137C.
- *Length.*—6.5-7.5 cm.
- *Width.*—5.3-7.2 cm.
- *Shape.*—Ovate.
- *Base shape.*—Attenuate to truncate.
- *Apex shape.*—Obtuse.
- *Margin.*—Lobed and some serrated.
- *Texture, upper surface.*—Puberlulent.
- *Lower surface.*—Puberlulent.
- *Color of veins, upper surface.*—RHS 138C.
- *Color of veins, lower surface.*—RHS 138B.
- *Pattern of veining.*—Palmate to Pinnate.
- *Petiole color.*—RHS 137A.
- *Length.*—2.0-2.6 cm.
- *Diameter.*—0.3-0.5 cm.
- *Texture.*—Puberlulent.

Stem:
- *Quantity of main branches per plant.*—3-4.
- *Color of stem.*—RHS 138A.
- *Length of stem.*—6.5-11 cm.
- *Diameter.*—0.35-0.45 cm.
- *Length of internodes.*—0.5-2.3 cm.
- *Texture.*—Puberlulent.
- *Color of peduncle.*—RHS 138A.
- *Length of peduncle.*—4.5-7.8 cm.
- *Peduncle diameter.*—0.2 cm.
- *Texture.*—Puberlulent.

Inflorescence:
- *Type.*—Compositae type, solitary daisy-type inflorescences borne terminally above foliage, ray florets arranged acropetally on a capitulum.
- *Quantity of short days to flowering (response time).*—7.5 weeks.
- *Natural season flowering.*—Not determined on this variety.
- *Quantity of inflorescences per plant.*—12-15 flowers.
- *Lastingness of individual blooms on the plant.*—4 weeks.
- *Fragrance.*—Daisy like.

Bud (just when opening/showing color):
- *Color.*—RHS 2B.
- *Length.*—1.4 cm.
- *Width.*—1.0-1.2 cm.
- *Shape.*—Oblate.

Immature inflorescence:
- *Diameter.*—6.2 cm.
- *Color of ray florets, upper surface.*—RHS 5B.
- *Lower surface.*—RHS 5C.

Mature inflorescence:
- *Diameter.*—7.3-7.6 cm.
- *Depth.*—2.4-2.6 cm.
- *Total diameter of disc.*—1.6-1.8 cm.
- *Receptacle color.*—RHS 145B.
- *Receptable height.*—0.5 cm.
- *Receptacle diameter.*—0.7 cm.

Ray florets:
- *Average quantity of florets.*—21.
- *Color of ray florets, upper surface.*—RHS 5B.
- *Lower surface.*—RHS 5C.
- *Length.*—3.0-3.6 cm.
- *Width.*—1.3-1.5 cm.
- *Shape.*—Elliptical.
- *Apex shape.*—Acute.
- *Margin.*—Entire.
- *Texture, upper surface.*—Smooth.
- *Lower surface.*—Smooth.

Disc florets:
- *Average quantity of florets.*—210.
- *Color of florets.*—RHS 5A.
- *Length.*—0.5-0.6 cm.
- *Width.*—0.15 cm.
- *Shape.*—Tubular, elongated.
- *Apex shape.*—Acute, 5 pointed.

Phyllaries:
- *Quantity.*—23-25.
- *Color, upper surface.*—RHS 139A.
- *Lower surface.*—RHS 137A.
- *Length.*—1.0-1.2 cm.
- *Width.*—0.25-0.4 cm.
- *Shape.*—Lanceolate.
- *Apex shape.*—Acute.
- *Base.*—Fused.
- *Margins.*—Entire; slightly papery.
- *Texture, upper surface.*—Hair.
- *Lower surface.*—Smooth.

Reproductive organs:
- *Pistil.*—1, found on both types of florets.
- *Length.*—0.7 cm.
- *Style color.*—RHS 150C.
- *Style length.*—0.5 cm.
- *Stigma color.*—RHS 1C.
- *Stigma shape.*—Bi-parted.
- *Ovary color.*—RHS 155C but more translucent.
- *Stamens.*—4, found only on the disc florets.
- *Color of filaments.*—RHS 155C.
- *Length filaments.*—0.4 cm.
- *Anther color.*—RHS 1A.
- *Anther length.*—0.1 cm.
- *Anther shape.*—Oval.
- *Color of pollen.*—Absent.
- *Pollen amount.*—Absent.
- *Fertility/seed set.*—Has not been observed to date.
- *Disease/pest resistance.*—Has not been observed to date.

What is claimed is:

1. A new and distinct variety of *Chrysanthemum* plant named 'CIDZ0118' substantially as illustrated and described herein.

* * * * *